(12) United States Patent
Miyamoto et al.

(10) Patent No.: US 9,481,882 B2
(45) Date of Patent: Nov. 1, 2016

(54) CONSTITUTION OF TOOL FOR ANALYZING BIOMOLECULAR INTERACTION AND ANALYSIS METHOD USING SAME

(75) Inventors: Etsuko Miyamoto, Tokyo (JP); Toru Tsuji, Tokyo (JP); Shigeo Fujimori, Tokyo (JP); Masamichi Ishizaka, Gyeongsangbuk-do (KR)

(73) Assignee: TOKYO UNIVERSITY OF SCIENCE FOUNDATION, Tokyo (JP)

( * ) Notice: Subject to any disclaimer, the term of this patent is extended or adjusted under 35 U.S.C. 154(b) by 335 days.

(21) Appl. No.: 13/638,203

(22) PCT Filed: Mar. 31, 2011

(86) PCT No.: PCT/JP2011/058203
§ 371 (c)(1),
(2), (4) Date: Dec. 12, 2012

(87) PCT Pub. No.: WO2011/125833
PCT Pub. Date: Oct. 13, 2011

(65) Prior Publication Data
US 2013/0196331 A1    Aug. 1, 2013

(30) Foreign Application Priority Data
Mar. 31, 2010    (JP) .................................. 2010082991

(51) Int. Cl.
C12N 15/10    (2006.01)
C12N 15/64    (2006.01)
G01N 33/53    (2006.01)

(52) U.S. Cl.
CPC ....... *C12N 15/1055* (2013.01); *C12N 15/1062* (2013.01); *C12N 15/1096* (2013.01); *C12N 15/64* (2013.01); *G01N 33/5308* (2013.01)

(58) Field of Classification Search
None
See application file for complete search history.

(56) References Cited

U.S. PATENT DOCUMENTS

| 5,082,773 A | 1/1992 | Fahnestock |
| 2002/0072087 A1 | 6/2002 | Yanagawa et al. |
| 2004/0018536 A1 | 1/2004 | Yanagawa et al. |

FOREIGN PATENT DOCUMENTS

| EP | 1 304 386 | 4/2003 |
| EP | 1 431 386 | 6/2004 |
| EP | 1 854 883 | 11/2007 |
| JP | 3-501801 | 4/1991 |
| JP | 2002/176987 | 6/2002 |
| WO | 98/16636 | 4/1998 |
| WO | 03/048363 | 6/2003 |
| WO | 2005/089285 | 9/2005 |

OTHER PUBLICATIONS

Bautz et al., The influence of noncomplementary bases on the stability of ordered polynucleotides; PNAS, vol. 52, pp. 1476-1481, 1964.*
International Preliminary Report on Patentability and Written Opinion issued Nov. 22, 2012 in International (PCT) Application No. PCT/JP2011/058203.
International Search Report mailed Jul. 5, 2011 in corresponding International Application No. PCT/JP2011/058203.
Miyamoto-Sato et al.; "Cell-free Cotranslation and Selection Using in Vitro virus for High-Throughput Analysis of Protein—Protein Interactions and Complexes"; Genome Research; vol. 15, pp. 710-717; 2005.
Fullwood et al.; "Next-Generation DNA Sequencing of Paired-End Tags (PET) for Transcriptome and Genome Analyses"; Genome Research; vol. 19; pp. 521-532; 2009.
Kosugi et al.; "Six Classes of Nuclear Localization Signals Specific to Different Binding Grooves of Importin α"; The Journal of Biological Chemistry; vol. 284; No. 1; pp. 478-485; 2009.
Miyamoto-Sato et al.; "A Comprehensive Resource of Interacting Protein Regions for Refining Human Transcription Factor Networks"; PLoS ONE; vol. 5, Issue 2; e9289; pp. 1-11; 2010.
Extended European Search Report issued Apr. 16, 2014 in corresponding European Application No. 11 76 5733.8.
Stump et al., "SP6 RNA polymerase efficiently synthesizes RNA from short double-stranded DNA templates", Nucleic Acids Research, 1993, vol. 21, No. 23, pp. 5480-5484.
Melton et al., "Efficient in vitro synthesis of biologically active RNA and RNA hybridization probes from plasmids containing a bacteriophage SP6 promoter", Nucleic Acids Research, 1984, vol. 12, No. 18, pp. 7035-7056.

* cited by examiner

*Primary Examiner* — Addison D Ault
(74) *Attorney, Agent, or Firm* — Wenderoth, Lind & Ponack, L.L.P.

(57) ABSTRACT

A method for analyzing biomolecular interactions, which method can be carried out without performing affinity selection using an immobilized bait, is provided. mRNA portions of assignment molecules that interacted with each other are linked together by annealing via a DNA linker for linking mRNA portions of assignment molecules together, the DNA linker comprising, at the 5'-end, an mRNA-complementary region complementary to a sequence at the 5'-end of each mRNA portion, and, at the 3'-end, a self-complementary region complementary between molecules of the DNA linker, the DNA linker being phosphorylated at the 5'-end.

2 Claims, 7 Drawing Sheets

GAATTTAGGTGACACTATAGAAACAATTACTATTTACAATTACAATGGCTAGCATGACTGGTGGACAGCAAATGGGAGGC
CGAGCGCA··· (SEQ ID NO: 1)

Fig. 3

ACCAGTCATGCTAGC<u>CAT</u>TGTAATTGTAAATAGTAATTGTTTCTATAGTGTCACCTAAATTCGGCGCGCCGGCGCGCC
(SEQ ID NO: 2)

Fig. 6 priSqlinker07-02: CTATTTACAATTACAATGGCTAGCATGACT (SEQ ID NO: 3)
priFOS211FLAGA6r: TTTTTT CTT ATC GTC GTC ATC TTT GTA GTC GCC CAG
GTC ATC AGG GAT C (SEQ ID NO: 5)

Fig. 7

*TTCGCCCTT* CTA TTT ACA ATT ACA <u>ATG</u> GCT AGC ATG ACT GGT GGA CAG CAA ATG GGA
GGC CGA GCG CAN AGC ATT GGC AGG AGG GGC AAG GTG AAA CAG TTN TCT CCA GAA
GAA GAA GAG AAA AGG AGA ATC CGA AGG GAA AGG AAT AAN ATG GCT GCA GCC AAA
TGC CGC ANC CGG AGG AGG GAG CTG ACT GAT ACA CTC CAA GCG GAG ACA GAC CAA
CTA GAA GAT GAG AAG TCT GCT TTG CAG ACC GAG ATT GCC AAC CTG CTG AAG GAG
AAG GAA AAA CTA GAG TTC ATC CTG GCA GCT CAC CGA CCT GCC TGC AAG ATT CCT
GAT GAC CTG GGC GAC TAC AAA GAT GAC GAC GAT AAG *AAAAAAAAGGGCGAA*

(SEQ ID NO: 4)

Fig. 8

Fig. 9 a Sqlinker 08

TTGTTTCTATAGTGTCACCTAAATTC GGCGCGCCGGCGCGCC  (SEQ ID NO: 6)

b priFOS1r

CATCTTATTCCTTTCCCTTCGGATTC  (SEQ ID NO: 7)

c priSqlinker0801f

TTGTTTCTATAGTGTCACCTAAATTCG  (SEQ ID NO: 8)

d
TTGTTTCTATAGTGTCACCTAAATTCGGCGCGCCGGCGCGCCGAATTTAGGTGACACTATAGAAACAA
GAATTTAGGTGACACTATAGAAACAATTACTATTTACAATTACAATGGCTAGCATGACTGGTGGACAGC
AAATGGGAGGCCGAGCGCAGAGCATTGGCAGGAGGGGCAAGGTGGAACAGTTATCTCCAGAAGAAG
AAGAGAAAAGGAGAATCCGAAGGGAAAGGAATAAGATG (SEQ ID NO: 9)

e priFLAGA6r

TTTTTTCTTATCGTCGTCATCTTTGTAGTC  (SEQ ID NO: 10)

CONSTITUTION OF TOOL FOR ANALYZING BIOMOLECULAR INTERACTION AND ANALYSIS METHOD USING SAME

TECHNICAL FIELD

The present invention relates to a constitution of a biomolecular-interaction analysis tool and an analysis method using it.

BACKGROUND ART

Attempts are being made to introduce a next-generation sequencer to transcriptome and proteome analysis, to obtain a large amount of information on intermolecular interactions of protein/DNA/RNA (Non-patent Document 1).

Figure 1:
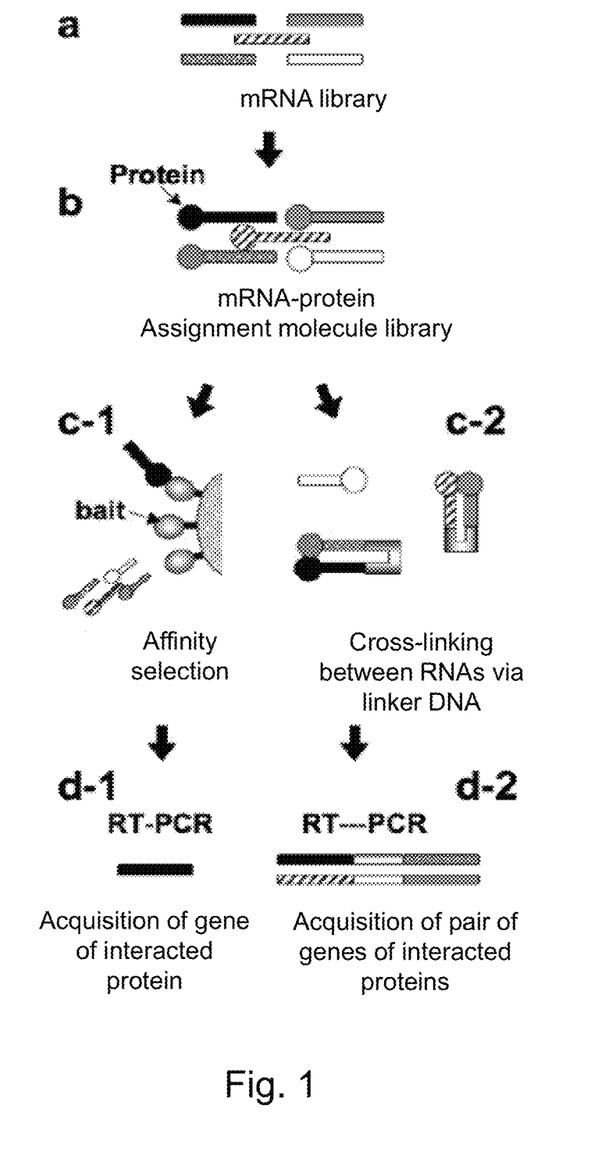
FIG. 1 shows comparison between the conventional IVV method (panels a, b, c-1 and d-1) and the method of the present invention (panels a, b, c-2 and d-2). Panel a shows an mRNA library; panel b shows an mRNA-protein library; panel c-1 shows affinity selection using a target protein (bait)

A method wherein mRNA-protein assignment molecules prepared by linking mRNAs to the proteins encoded thereby via a covalent bond are used (FIG. 1, panels a and b) to obtain the amino acid sequence information of the protein as the nucleotide sequence information of DNA is known as the in vitro virus (IVV) method (Patent Document 1 and Patent Document 2). By using the IVV method and a Sanger-type DNA sequencer, proteome analysis has been carried out (Non-patent Document 2, Non-patent Document 3 and Non-patent Document 4). However, conventional methods need immobilization of a target protein (called a "bait") on a resin for performing affinity selection (FIG. 1, panel c-1), followed by amplification of DNA by RT-PCR from mRNA linked to a protein bound to the bait (FIG. 1, panel d-1). Therefore, large-scale analysis has been in need of preparation of a large amount of baits which are to be individually subjected to affinity selection.

For example, in cases where interactions of 50 types of bait proteins were to be analyzed, it has been necessary to individually prepare the 50 types of proteins and immobilize these on a resin, followed by performing affinity selection. Such an operation is laborious and costly. Further, even if only about 50 types of bait proteins were used, the number of the obtained interactions cannot be said to be comprehensive.

PRIOR ART DOCUMENTS

Patent Documents

Patent Document 1: WO 98/16636
Patent Document 2: WO 2003/048363

Non-Patent Documents

Non-patent Document 1: Genome Res, 19, 521-532, 2009
Non-patent Document 2: Genome Res., 15, 710-717, 2005
Non-patent Document 3: J Biol Chem, 284, 478-485, 2009
Non-patent Document 4: PLoS ONE, 5, e9289, 2010

SUMMARY OF THE INVENTION

Problems to be Solved by the Invention

The present invention aims to provide a method for analyzing biomolecular interactions, which does not require affinity selection using an immobilized bait.

Means for Solving the Problems

The present inventors discovered that the mRNA portions of mRNA-protein assignment molecules that become close to each other when the protein portions of the assignment molecules interacted with each other can be cross-linked to each other by using an oligo DNA linker having a specific structure, thereby completing the present invention.

The present invention provides a DNA linker for linking mRNA portions of assignment molecules together, the DNA linker comprising, at the 5'-end, an mRNA-complementary region complementary to a sequence at the 5'-end of each mRNA portion, and, at the 3'-end, a self-complementary region complementary between molecules of the DNA linker, the DNA linker being phosphorylated at the 5'-end. The sequence at the 5'-end of the mRNA portion of each assignment molecule may comprise, from the 5'-end side, a promoter sequence, Ω-like sequence and T7 peptide tag gene in this order.

The present invention further provides a method for synthesizing DNA in which genes encoding proteins having interaction with each other are linked together, the method comprising the steps of:

allowing interaction between assignment molecules at protein portions thereof;

linking mRNA portions of the assignment molecules that showed interaction with each other together via the DNA linker of the present invention by annealing, wherein pairing occurs between the sequence at the 5'-end of each mRNA portion and the mRNA-complementary region, and between the self-complementary regions;

performing reverse transcription to convert the mRNA portions into DNA-RNA hybrids;

linking the 5'-end of the DNA linker to the 3'-end of the DNA strand synthesized by the reverse transcription;

degrading RNA constituting the DNA-RNA hybrids; and extending the 3'-end of the DNA linker to synthesize cDNA.

The present invention further provides a method for analyzing interaction, the method comprising determining the nucleotide sequence of DNA obtained by the synthesis method of the present invention and identifying the combination of the genes encoding the proteins having interaction with each other or the combination of the proteins having interaction with each other.

Effect of the Invention

By the present invention, a method for analyzing biomolecular interaction, which does not require affinity selection using an immobilized bait, is provided. By converting the amino acid sequences of proteins into the nucleotide sequences of DNAs, and by carrying out this analysis using a next-generation sequencer, protein-protein interactions can be comprehensively analyzed. In addition, preparation of bait proteins is not necessary, and all the mRNA-protein assignment molecules existing in a library can be used as baits. In the case of human, since the number of types of protein-protein interactions are estimated to be about 300,000 (Rhodes et al., Nat. Biotech. 2005) and the analytical capacity of the next-generation sequencer is 500,000 to 100,000,000 reads/run, all the protein-protein interactions are detected at once according to expectation.

BRIEF DESCRIPTION OF THE DRAWINGS

presented on a resin; and panel d-1 shows reverse transcription-PCR for obtaining the gene encoding a protein bound to the bait. In the method of the present invention, selection using a bait is not carried out. Panel c-2 shows that, since RNAs linked to proteins having interaction with each other become close to each other, the RNAs are cross-linked to each other via a linker DNA. Panel d-2 shows that, by several steps of the reaction followed by PCR, a DNA fragment wherein the genes encoding two types of proteins having interaction with each other are linked together via the linker can be obtained. Many types of interactions can be detected at once.

EMBODIMENT FOR CARRYING OUT THE INVENTION

<1> DNA Linker of Present Invention

The DNA linker of the present invention is a DNA linker for linking the mRNA portions of assignment molecules together, and has, at the 5'-end, an mRNA-complementary region complementary to a sequence at the 5'-end of each mRNA portion, and, at the 3'-end, a self-complementary region complementary between molecules of the DNA linker, the DNA linker being phosphorylated at the 5'-end.

As the assignment molecules, conventional assignment molecules may be used as described later. Examples of the assignment molecules include those having, as the sequence at the 5'-end of the mRNA portion of each assignment molecule, a promoter sequence, Ω-like sequence and T7 peptide tag gene from the 5'-end side in this order. The promoter portion is not restricted as long as it has a promoter sequence that allows in vitro transcription reaction, and the SP6 promoter portion is not restricted as long as it has a promoter sequence that allows in vitro transcription reaction. For example, the T7 promoter can also be used. The Ω-like sequence portion is not restricted as long as it enhances translation efficiency. The T7-tag portion is not restricted as long as it is a peptide tag.

As the sequence of the mRNA-complementary region of the DNA linker of the present invention, a sequence complementary to the sequence at the 5'-end of the mRNA portion of the assignment molecule used may be selected. The length of the mRNA-complementary region is usually 8 to 30 bp, preferably 10 to 20 bp. The Tm value of this region is usually 20 to 70° C., preferably 25 to 50° C.

The self-complementary region of the DNA linker of the present invention is not restricted as long as the 3'-ends of linkers can be paired with each other by a complementary sequence. The region has a length of usually 10 to 35 bp, preferably 12 to 30 bp. The Tm value of this region is usually 22 to 72° C., preferably 25 to 55° C.

A spacer DNA may be inserted between the self-complementary region and the mRNA-complementary region. The length of the spacer is usually 3 to 15 bp, preferably 4 to 10 bp.

<2> Method of DNA Synthesis of Present Invention

The method of DNA synthesis of the present invention is a method for synthesizing DNA in which the genes encoding proteins having interaction with each other are linked together, the method comprising the steps of:

(1) allowing interaction between assignment molecules at protein portions thereof;

(2) linking mRNA portions of the assignment molecules that showed interaction with each other together via the DNA linker of the present invention by annealing, wherein pairing occurs between the sequence at the 5'-end of each mRNA portion and the mRNA-complementary region, and between the self-complementary regions;

(3) performing reverse transcription to convert the mRNA portions into DNA-RNA hybrids;

(4) linking the 5'-end of the DNA linker to the 3'-end of the DNA strand synthesized by the reverse transcription;

(5) degrading RNA constituting the DNA-RNA hybrids; and (6) extending the 3'-end of the DNA linker to synthesize cDNA.

Each of the steps is described below.

1) Interaction

The conditions for the interaction are not restricted as long as the interaction between the protein portions of assignment molecules is maintained during the annealing process in the subsequent step. Examples of the conditions for the interaction include those described in Patent Document 2. Assignment molecules synthesized by a cell-free translation system may be mixed together, or, as described later, coding molecules may be translated (cotranslated) in a single system.

2) Annealing

The mRNA portions of assignment molecules that showed interaction are linked together via the DNA linker described in claim 1 or 2 by annealing. The pairing may occur between the 5'-end sequence of each mRNA portion and the mRNA-complementary region, and between self-complementary regions. These pairings may occur at the same time, or one of these may precede the other. In cases where the pairings are allowed to occur at the same time, the Tm values of the regions are set close to each other (with a difference of usually not more than 5° C.). Alternatively, the region having a higher Tm may first be paired, followed by pairing of the other region. For example, the self-complementary regions of DNA linkers may be paired with each other in a separate system, and the paired DNA linker may then be added to the system for the interaction, to allow paring of the sequence at the 5'-end of the mRNA portion of each assignment molecule with the mRNA-complementary region.

Since the DNA linkers are more prone to form a hybrid in advance using their self-complementary regions, Tms≥Tmr is preferably satisfied, wherein Tms represents the Tm value of the self-complementary region and Tmr represents the Tm value of the mRNA region. Further, since the reactions in the later steps need to be carried out at the temperature at which the reverse transcription reaction and extension reaction are carried out (e.g., 37° C.), Tmr>enzyme reaction temperature needs to be satisfied.

For the annealing, the DNA linker is added usually at a concentration of 10 fM to 10 μM, preferably at a concentration of 50 fM to 5 μM.

3) Reverse Transcription

By reverse transcription, the mRNA portions are converted into DNA-RNA hybrids. The reverse transcription may be carried out under normal conditions.

4) Ligation Reaction

The 5'-end of each DNA linker is linked to the 3'-end of the DNA strand synthesized by reverse transcription. The ligation reaction may be carried out under normal conditions.

5) Degradation of RNA

RNA in the DNA-RNA hybrid is degraded. This may be carried out using RNase H.

6) Extension Reaction

Using the DNA linker as a primer, extension can be carried out with DNA polymerase under normal conditions.

The extended DNA may be purified and amplified by normal cloning or normal PCR.

Figure 2:
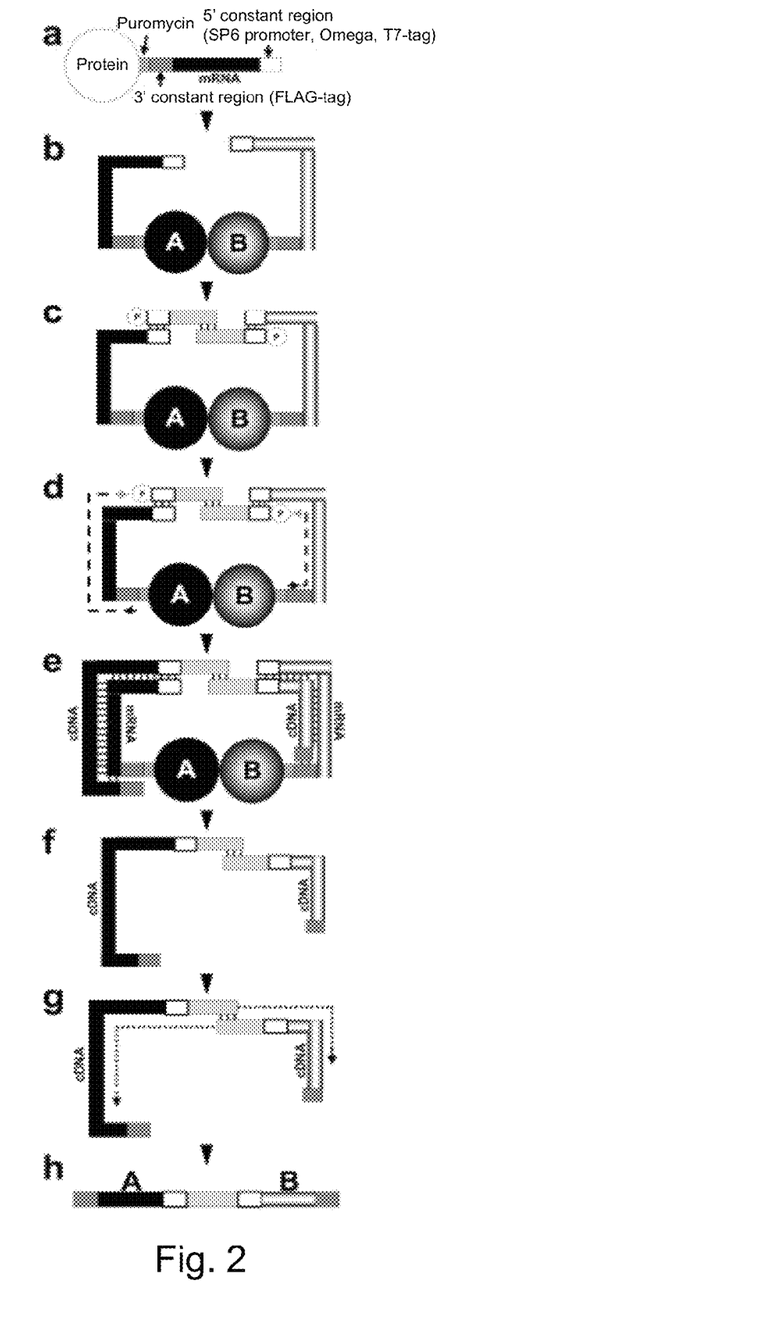
FIG. 2 is a diagram for describing the method of the present invention for synthesizing DNA having a sequence in which genes are linked together.

FIG. 2 shows a scheme of the synthesis method of the present invention. As in the conventional IVV method, the C-terminus of the protein is linked to the mRNA via puromycin. Each of the 5'-end and 3'-end of the mRNA has a constant region. For example, for the 5'-constant region, a promoter sequence, Omega sequence for enhancement of the translation efficiency, and/or the like may be used. For the 3'-end, an affinity tag such as the FLAG peptide may be used (a). A library of such mRNA-protein assignment molecules is constructed from an mRNA library. The 5'-ends of the mRNA portions of assignment molecules having protein-protein interaction become close to each other with high probability (b). Here, for linking the two IVVs that became close to each other, linking of nucleic acids in the same direction is necessary (square reaction), and this cannot be achieved by the conventional simple method for linking nucleic acids in the reverse direction. Therefore, an oligo DNA having a self-complementary sequence and a sequence complementary to the 5'-end of the mRNA is added, and the oligo DNA is allowed to function as a linker that cross-links the 5'-ends of mRNAs (c). Here, for enabling the ligation reaction in (e), a phosphate group is added to the 5'-end of the linker oligo DNA. Thereafter, reverse transcription reaction is performed using a primer complementary to the 3'-end of the mRNA (d). Subsequently, using DNA ligase, the extended cDNA is linked to the linker DNA (e). By this, preparation of the mRNA/cDNA hybrid is achieved. Thereafter, using RNase H, the RNA portions are degraded (f). The reaction of extension of the 3'-ends of the cDNAs is then performed using DNA polymerase (g). After completion of the extension reaction, a DNA fragment as shown in (h) is obtained, wherein the genes of the protein A and protein B that interact with each other are linked together via linker DNAs. By analyzing this DNA fragment with a sequencer, the protein-protein interaction can be read as the nucleotide sequence information of DNA.

<3> Analysis Method of Present Invention

By determination of the nucleotide sequence of the DNA obtained by the synthesis method of the present invention, the combination of the genes encoding the proteins that have interacted with each other or the combination of the proteins that have interacted with each other can be identified. By this, the interaction can be analyzed.

The determination of the nucleotide sequence may be carried out after cloning of the DNA. In case of sequencing by the Sanger method, by once carrying out cloning, even DNA fragments having the same length can be separated from each other, so that sequencing of the individual sequences can be carried out. Further, it is also possible to include a restriction site in the spacer and preliminarily digesting the DNA, followed by performing PCR, cloning and sequencing. The sequencing may also be carried out using a next-generation sequencer.

In the analysis method of the present invention, affinity selection using a bait does not need to be carried out. As shown in FIG. 1, panel c-2, interaction of proteins makes the linked RNAs become close to each other, which then allows cross-linking via an oligo DNA linker. In this step, in the present invention, nucleic acids need to be linked to each other in the same direction, unlike the cases of normal linking between nucleic acids (FIG. 1, panel c-2; square reaction). This can be achieved by a specific combination of several steps. By this, a DNA fragment in which the genes encoding proteins having interaction with each other are linked together via a linker can be obtained (FIG. 1, panel d-2). Thereafter, an mRNA-protein assignment molecule library may be constructed from a cDNA library to perform further analysis. Since preparation of a bait is not necessary and the steps of immobilization to resin beads and washing are also not necessary, the analysis of interaction can be remarkably efficiently carried out. Further, all the interactions existing in the library can be identified at once. Therefore, a large amount of interaction data can be obtained and the capacity of the next-generation sequencer can be fully utilized to perform the analysis.

<4> Assignment Molecule

In the present description, the assignment molecule means a molecule that assigns the phenotype and the genotype to each other. The assignment molecule is composed of a genotype molecule comprising a nucleic acid having a nucleotide sequence reflecting the genotype and a phenotype molecule comprising a protein involved in expression of the phenotype, which genotype molecule and phenotype molecule are linked to each other. The genotype molecule is composed of a nucleotide sequence reflecting the genotype in a form that allows translation of the nucleotide sequence, and a spacer portion linked thereto. Since such an assignment molecule is described in, for example, Patent Document 2, the molecule will be described below by reference to Patent Document 2. It should be noted that, since, in the present invention, the interaction can be judged by determination of the sequence of the linked DNA, the modification or labeling for detection of the interaction in Patent Document 2 is not necessary in the present invention.

In the assignment molecule, the portion derived from the phenotype molecule, the portion derived from the spacer molecule and the portion derived from the coding molecule are referred to as the decoded portion, spacer portion and coding portion, respectively. Further, in the genotype molecule, the portion derived from the spacer molecule and the portion derived from the coding molecule are referred to as the spacer portion and the coding portion, respectively.

FIG. 8 in Patent Document 2 roughly shows examples of the constitutions of the assignment molecule, spacer molecule and coding molecule. This assignment molecule is composed of the spacer (referred to as the spacer portion) and the nucleotide sequence reflecting the code of the phenotype (referred to as the coding portion). The assignment molecule has a constitution prepared by linking the spacer portion comprising puromycin to the coding molecule by a certain method to provide the genotype molecule, which is then linked to the phenotype molecule on the ribosome in a cell-free translation system. The spacer molecule is composed of: the PEG region whose main component is polyethylene glycol; the CCA region comprising at least puromycin, or puromycin and DNA and/or RNA having 1 or more residues; the donor region comprising at least DNA and/or RNA having 1 or more residues; and the functionalization unit (X) in which the base of at least one residue of DNA and/or RNA is functionally modified. The coding molecule is constituted by: the 3'-end region which is composed of a part of the sequence of the decoded portion and comprises a poly(A) sequence of DNA and/or RNA; 5'-UTR which is composed of DNA and/or RNA and comprises a transcription promoter and a translation enhancer; and the ORF region mainly composed of the sequence of the phenotype molecule. A description is given below by reference to this example, but the present invention is not restricted to the example.

<4-1> Spacer Molecule

The spacer molecule comprises: the donor region which can be bound to the 3'-end of nucleic acid; the PEG region which is mainly composed of polyethylene glycol; and the peptide acceptor region which comprises a group that can be bound to a peptide by transpeptidation.

The donor region which can be bound to the 3'-end of nucleic acid is normally composed of 1 or more nucleotides. The number of nucleotides is usually 1 to 15, preferably 1 to 2. The nucleotides may be either ribonucleotides or deoxyribonucleotides.

The sequence at the 5'-end of the donor region influences the ligation efficiency. For ligation between the coding portion and the spacer portion, the sequence needs to comprise at least 1 residue. For the acceptor having a poly(A) sequence, the sequence at the 5'-end of the donor region preferably comprises at least 1 residue of dC (deoxycytidylic acid) or the 2 residues dCdC (dideoxycytidylic acid). The order of preference of the type of the base is as follows: C>U/T>G>A.

The PEG region comprises polyethylene glycol as the major component. The term "comprises as the major component" herein means that the total number of nucleotides contained in the PEG region is not more than 20 bp, or the average molecular weight of the polyethylene glycol is not less than 400. The term preferably means that the total number of nucleotides is not more than 10 bp, or the average molecular weight of the polyethylene glycol is not less than 1,000.

The average molecular weight of the polyethylene glycol in the PEG region is usually 400 to 30,000, preferably 1,000 to 10,000, more preferably 2,000 to 8,000. In cases where the molecular weight of the polyethylene glycol is less than about 400, assignment translation of the genotype molecule comprising the spacer portion derived from this spacer molecule may require posttreatment after the assignment translation in some cases (Liu, R., Barrick, E., Szostak, J. W., Roberts, R. W. (2000) Methods in Enzymology, vol. 318, 268-293). On the other hand, in cases where PEG having a molecular weight of not less than 1,000, preferably not less than 2,000 is used, the assignment can be achieved highly efficiently only by assignment translation, so that posttreatment after the translation is not necessary. Further, as the molecular weight of the polyethylene glycol increases, the stability of the genotype molecule tends to increase. In cases where the molecular weight is not less than 1,000, the stability is especially excellent, while in cases where the molecular weight is not more than 400, the properties are not largely different from those of a DNA spacer, leading to instability in some cases.

The peptide acceptor region is not restricted as long as it can be bound to the C-terminus of a peptide, and examples of the region which may be used include puromycin, 3'-N-aminoacylpuromycin aminonucleoside (PANS-amino acid), such as PANS-Gly, wherein the amino acid portion is glycine; PANS-Val, wherein the amino acid portion is valine; PANS-Ala, wherein the amino acid portion is alanine; and PANS-all amino acids, which corresponds to all the amino acids. Further, 3'-N-aminoacyladenosine aminonucleoside (AANS-amino acid) in which the amino group of 3'-aminoadenosine is chemically bound to the carboxyl group of an amino acid via an amide bond formed as a result of dehydration condensation, such as AANS-Gly, wherein the amino acid portion is glycine; AANS-Val, wherein the amino acid portion is valine; AANS-Ala, wherein the amino acid portion is alanine; and AANS-all amino acids, which corresponds to all the amino acids; may be used. Further, a nucleoside or a nucleoside bound to an amino acid via an ester bond may also be used. Further, any compound having a binding mode that allows chemical binding of a substance comprising a nucleoside or a chemical structural skeleton similar to a nucleoside with a substance comprising an amino acid or a chemical structural skeleton similar to an amino acid may be used.

The peptide acceptor region is preferably composed of puromycin or a derivative thereof, or puromycin or a derivative thereof and 1 residue or 2 residues of deoxyribonucleotide(s) or ribonucleotide(s). The derivative herein means a derivative that can be bound to the C-terminus of a peptide in a protein translation system. The puromycin derivative is not restricted to one having the complete puromycin structure, and also includes one which partially lacks the puromycin structure. Specific examples of the puromycin derivative include PANS-amino acids and AANS-amino acids.

The peptide acceptor region may have a structure which comprises only puromycin, but the region preferably has in its 5'-side a nucleotide sequence of DNA and/or RNA having 1 or more residues. Preferred examples of the sequence include sequences of dC-puromycin and rC-puromycin, and more preferred examples of the sequence include sequences of dCdC-puromycin, rCrC-puromycin, rCdC-puromycin and dCrC-puromycin. As the sequence, a CCA sequence that mimics the 3'-end of an aminoacyl-tRNA (Philipps, G. R. (1969) Nature 223, 374-377) is suitable. The order of preference of the type of the base is as follows: C>U/T>G>A.

<4-2> Coding Molecule

The coding molecule is a nucleic acid comprising: the 5'-untranslated region comprising a transcription promoter and a translation enhancer; the ORF region which is linked to the 3'-side of the 5'-untranslated region and encodes a protein; and the 3'-end region which is linked to the 3'-side of the ORF region and comprises a poly(A) sequence and, as required, a translation-enhancing sequence (e.g., sequence recognized by the restriction enzyme XhoI) at the 5'-side of the poly(A) sequence.

The coding molecule may be either DNA or RNA, and, in cases of RNA, a Cap structure may be either present or absent at the 5'-end. Further, the coding molecule may be incorporated in an arbitrary vector or plasmid.

The 3'-end region preferably comprises an SNNS sequence (e.g., XhoI sequence) which is followed by a poly(A) sequence in its downstream. As a factor that influences the efficiency of ligation between the spacer molecule and the coding molecule, the poly(A) sequence in the 3'-end region is important. The poly(A) sequence is a continuous poly(A) strand having at least 2 residues of dA and/or rA, and may be either composed of only one of these types of residues or a mixture of these. The sequence is a strand of continuous poly(A) having preferably not less than 3 residues, more preferably not less than 6 residues, still more preferably not less than 8 residues.

Examples of factors that affect the efficiency of translation of the coding molecule include the combination of the 5'-UTR, which is composed of the transcription promoter and the translation enhancer, and the 3'-end region comprising the poly(A) sequence. The effect of the poly(A) sequence in the 3'-end region is usually produced with 10 residues or less. The transcription promoter in the 5'-UTR is not restricted and may be T7/T3, SP6 or the like. The transcription promoter is preferably SP6, which is especially preferably used in cases where a sequence comprising an omega sequence or a part of an omega sequence (Ω-like sequence) is employed. The translation enhancer is preferably a part of an omega sequence, and the part of an omega sequence preferably comprises a part (O29) of the omega sequence in TMV (Gallie D. R., Walbot V. (1992) Nucleic Acids Res., vol. 20, 4631-4638).

Further, for high translation efficiency, the combination of the XhoI sequence and the poly(A) sequence in the 3'-end region is important. The combination of the part downstream of the ORF region, that is, the XhoI sequence and the affinity tag in the upstream thereof, and the poly(A) sequence is also important. The sequence of the affinity tag is not restricted as long as it is a sequence for using a method for allowing detection of a protein, such as the antigen-antibody reaction. The sequence is preferably the Flag-tag sequence, which is a tag for affinity separation analysis by the antigen-antibody reaction. In terms of the effect of the poly(A) sequence, the translation efficiency can be increased by using an affinity tag such as the Flag-tag together with the XhoI sequence, and by further using the poly(A) sequence attached thereto.

The above constitution effective for increasing the translation efficiency is also effective for increasing the assignment efficiency.

The sequence of the ORF region may be any sequence composed of DNA and/or RNA. The sequence is not restricted, and examples of the sequence include gene sequences, exon sequences, intron sequences and random sequences, and arbitrary natural and artificial sequences. By using SP6+O29 for the 5'-UTR of the coding molecule and Flag+XhoI+A. (n=8) for the 3'-end region, the lengths of the 5'-UTR and the 3'-end region become about 60 bp and about 40 bp, respectively, allowing their incorporation into a PCR primer to provide adaptor regions.

Therefore, a coding molecule having the 5'-UTR and the 3'-end region can be simply prepared by PCR from an arbitrary vector, plasmid or cDNA library. The coding molecule may allow translation to proceed beyond the ORF region. That is, the ORF region does not need to have a stop codon at its end.

FIG. 10 in Patent Document 2 shows detailed constitution of an example of the coding molecule. The coding molecule is composed of the 3'-end region; 5'-UTR region comprising a transcription promoter and a translation enhancer composed of DNA and/or RNA; and the ORF region which is composed of the sequence information for the decoded portion, that is, which encodes the phenotype protein. Here, the 3'-end region comprises an affinity tag sequence, XhoI sequence and poly A sequence composed of DNA and/or RNA, and the Flag-tag sequence is used. For the 5'-UTR, SP6 as the transcription promoter, and O29, which is a part of the omega sequence, as the transcription enhancer are used.

<4-3> Genotype Molecule and Method of Production Thereof

The genotype molecule is formed by linking the 3'-end of the coding molecule to the donor region of the spacer molecule, which coding molecule is a nucleic acid comprising: the 5'-untranslated region comprising a transcription promoter and a translation enhancer; the ORF region which is linked to the 3'-side of the 5'-untranslated region and encodes a protein; and the 3'-end region which is linked to the 3'-side of the ORF region and comprises a poly A sequence.

The coding molecule constituting the genotype molecule is the same as described above about the coding molecule except that the XhoI sequence is not indispensable. However, the coding molecule preferably has the XhoI sequence.

The genotype molecule can be produced by linking the 3'-end of the above coding molecule to the donor region of the spacer molecule by normal ligase reaction. Examples of the reaction conditions normally include a temperature of 4 to 25° C. and a period of 4 to 48 hours, and, in cases where polyethylene glycol having the same molecular weight as the polyethylene glycol in the PEG region of the spacer molecule comprising the PEG region is added to the reaction system, the conditions may be a temperature of 15° C. and a reduced period of 0.5 to 4 hours.

Figure 10:
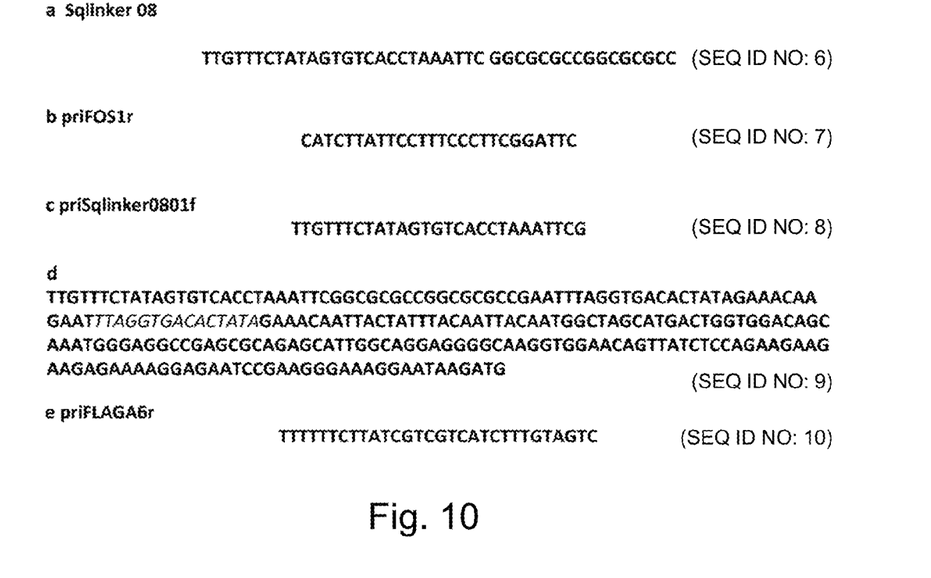
FIG. 10 shows the nucleotide sequences of the primers and the like used in Example 2 (a, SEQ ID NO:6; b, SEQ ID NO:7; c, SEQ ID NO:8; d, SEQ ID NO:9; e, SEQ ID NO:10).

The combination of the spacer molecule and the coding molecule has a large effect on the ligation efficiency. The 3'-end region of the coding portion, which corresponds to the acceptor, preferably has a poly(A) sequence of DNA and/or RNA comprising at least 2 residues, preferably not less than 3 residues, more preferably not less than 6 to 8 residues. Further, the translation enhancer in the 5'-UTR is preferably a partial sequence of the omega sequence (O29; FIG. 10 in Patent Document 2), and the donor region in the spacer portion preferably has at least 1 residue of dC (deoxycytidylic acid) or the 2 residues dCdC (dideoxycytidylic acid). By this, RNA ligase can be used to avoid problems in DNA ligase, and the efficiency can be maintained at 60 to 80%.

In cases where the genotype molecule is RNA, it is preferred to link (a) the 3'-end of the coding molecule comprising: the 5'-untranslated region comprising a transcription promoter and a translation enhancer; the ORF region which is linked to the 3'-side of the 5'-untranslated region and encodes a protein; and the 3'-end region which is linked to the 3'-side of the ORF region and comprises a poly A sequence; to (b) the donor region of the spacer molecule according to any one of (1) to (4), which region is composed of RNA; by RNA ligase in the presence of free polyethylene glycol having the same molecular weight as the polyethylene glycol constituting the PEG region in the spacer molecule.

By the addition, for the ligation reaction, of polyethylene glycol having the same molecular weight as the PEG region of the spacer portion comprising the PEG region, the ligation efficiency is increased to not less than 80 to 90% irrespective of the molecular weight of the polyethylene glycol in the spacer portion, and the separation step after the reaction can be omitted.

<4-4> Assignment Molecule and Method of Production Thereof

The assignment molecule is formed by linking, by transpeptidation, the above genotype molecule to the phenotype molecule, which is a protein encoded by the ORF region in the genotype molecule.

For example, the assignment molecule may be linked to the phenotype molecule, which is a protein encoded by the ORF region in the genotype molecule, by transpeptidation by translation of the genotype molecule in a cell-free translation system.

The cell-free translation system is preferably the wheat germ system or the rabbit reticulocyte system. The conditions for translation may be those usually employed. Examples of the conditions include a temperature of 25 to 37° C. for a period of 15 to 240 minutes.

In terms of the cell-free translation system, those of E. coli, rabbit reticulocytes and wheat germs have so far been studied for use in formation of assignment molecules, and formation of assignment molecules could be confirmed in only the rabbit reticulocyte system (Nemoto, N., Miyamoto-Sato, E., Yanagawa, H. (1997) FEBS Lett. 414, 405; Roberts, R. W, Szostak, J. W. (1997) Proc. Natl. Acad. Sci. USA 94, 12297). However, according to the present embodiment, the wheat germ system can also be used for formation of assignment molecules having the spacer portion comprising the PEG region. Further, although the rabbit reticulocyte system has been impractical because of instability of the genotype molecule and was therefore applied to only genotype molecules having short chain lengths (Roberts, R. W, Szostak, J. W. (1997) Proc. Natl. Acad. Sci. USA 94, 12297; Nemoto, N., Miyamoto-Sato, E., Yanagawa, H. (1997) FEBS Lett. 414, 405), assignment molecules having the spacer portion comprising the PEG region are more stable in the wheat germ system and allow handling of longer chains, making the system more practical.

By using various combinations of proteins synthesized by translation on ribosomes (assignment molecules) and their libraries, interactions among the proteins and substances can be analyzed in vitro, and this enables, for example, second screening for analysis of a detailed gene network after first screening of IVV (FIG. 21 in Patent Document 2)

In cases where an "interaction" is realized by cell-free cotranslation, the cell-free translation system may be any system including those of E. coli, rabbit reticulocytes and wheat germs. In the in vitro virus method (IVV method), the process of formation of the assignment molecule is rather instable in the E. coli system, but the process has been confirmed to be stable in the rabbit reticulocyte system (Nemoto N, Miyamoto-Sato E, Yanagawa H. (1997) FEBS Lett. 414, 405; Roberts R. W, Szostak J. W. (1997) Proc. Natl. Acad. Sci. USA 94, 12297) and even more stable in the wheat germ system (WO 02/46395).

Examples of the present invention are described below more specifically, but the Examples should be regarded merely as a help to specifically recognize the present invention. Therefore, the scope of the present invention is not restricted by the Examples below.

EXAMPLES

Example 1

Construction of F Gene mRNA

Figure 3:
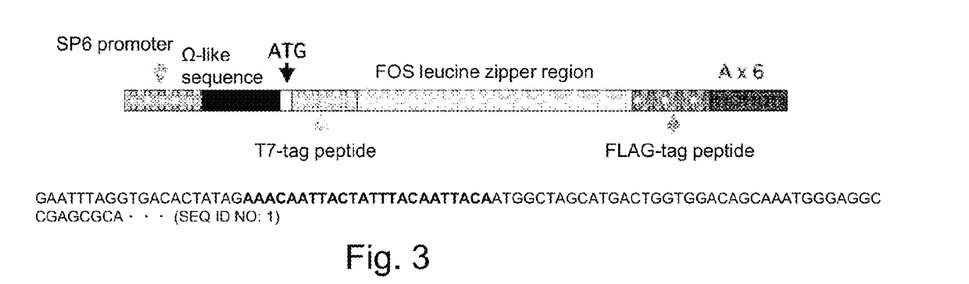
FIG. 3 shows a schematic diagram of the structure of the F gene mRNA used in Example 1 and the nucleotide sequence of priSP6O'T7FOS117f (SEQ ID NO:1). The nucleotide sequence corresponds to the region from the SP6 promoter to a part of the 5'-side of the FOS gene.

By PCR, the SP6 promoter, Ω-like sequence and a nucleotide sequence encoding the T7 tag peptide were linked to the 5'-side of a DNA fragment encoding a region comprising the leucine zipper structure of the human FOS protein. Further, a nucleotide sequence encoding the FLAG tag peptide and hexaadenylic acid were linked to the 3'-side, to construct an F gene DNA fragment. In this step, an oligo DNA (priSP6O'T7FOS117f (SEQ ID NO:1)) encoding the SP6 promoter, Ω-like sequence, T7 tag peptide and a part of the FOS gene was used as a forward primer. An oligo DNA (priFOS211FLAGA6r (SEQ ID NO:5)) encoding the hexaadenylic acid, FLAG tag and a part of the FOS gene was used as a reverse primer. These oligo DNAs were purchased from FASMAC Co., Ltd. PCR was performed using KOD Plus (TOYOBO) according to the manufacturer's instruction attached to the product. The thermal cycler was operated with the following program: 30 cycles of 94° C. for 30 seconds, 58° C. for 30 seconds and 68° C. for 30 seconds. As a template DNA, cDNA of the human FOS gene was used. Using the PCR product as a template, F gene mRNA was synthesized in vitro with SP6 RNA polymerase (Promega) (FIG. 3). The reaction was performed at 37° C. for 3 hours.

[Construction of DNA Linker]

Figure 4:
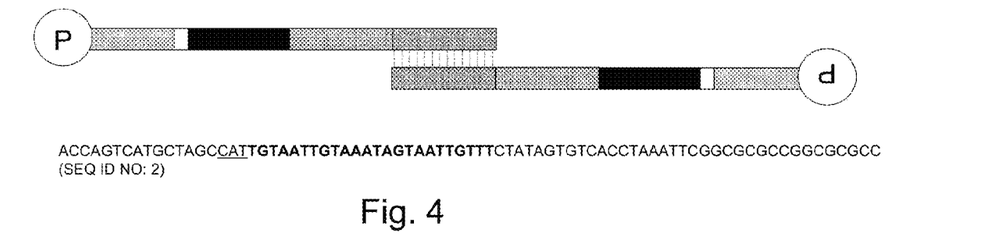
FIG. 4 shows a schematic diagram and the nucleotide sequence (SEQ ID NO:2) of the linker Sqlinker09 used in Example 1. The paired portion exhibits self-complementarity by a palindrome. The other portions correspond to the 5'-side of the mRNA shown in FIG. 3, that is, the SP6 promoter, Ω-like sequence and T7 peptide tag, whose sequences are expressed as those complementary to the sequences shown in FIG. 3.

A DNA linker (Sqlinker09) having a self-complementary region and a region complementary to the promoter sequence, Ω-like sequence and T7 peptide tag gene of the F gene mRNA constructed as described above was designed and synthesized (FIG. 4). A phosphate group was attached to the 5'-end of Sqlinker09. The oligo DNA was purchased from FASMAC Co., Ltd.

[Square Reaction]

(1) Annealing

With 20 pmol the F gene mRNA constructed as described above, 40 pmol of Sqlinker constructed as described above and 40 pmol of a primer for reverse transcription (priFOS211FLAGA6r) to be bound to the 3'-side of the F gene mRNA were mixed to prepare 10 µl of a solution. The solution was heated at 90° C. for 30 minutes and then gradually cooled to room temperature.

2) Reverse Transcription

With the solution prepared in 1), 10 µl of a mixed solution comprising reverse transcriptase, reaction buffer for reverse transcription and substrate dNTP mixture was mixed, and reverse transcription reaction was performed at 37° C. for 1 hour. As the reverse transcriptase, an M-MLV reverse transcriptase RNase H minus, point mutant manufactured by Promega was used.

3) Ligation Reaction

With the solution prepared in 2), 20 μl of a solution containing DNA ligase was mixed, and ligation reaction was performed at 25° C. for 1 hour. As the DNA ligase, Ligation high ver. 2 manufactured by TOYOBO was used.

4) RNA Degradation

To the solution prepared in 3), 1 μl of RNase H was mixed to degrade the RNA portion. As the RNase H, a product from Invitrogen was used.

5) Extension Reaction

To the solution prepared in 4), a mixed solution containing DNA polymerase, dNTP mix and a DNA polymerase reaction buffer was added, and extension reaction was performed at 56° C. for 15 minutes. In this reaction, the sample prepared in 4) was added in an amount described in Table 1.

6) PCR Reaction

To the reaction solution in 5), priFOS211FLAGA6r (20 pmol/μl) was added in an amount described in Table 1. The thermal cycler was operated with the following program: 40 cycles of 94° C. for 30 seconds, 56° C. for 30 seconds and 72° C. for 3 minutes.

primer, a DNA fragment having a length of 700 to 800 bp could be amplified. Thus, it is thought that a DNA fragment having the structure shown in FIG. 2h could be obtained.

Figure 6:
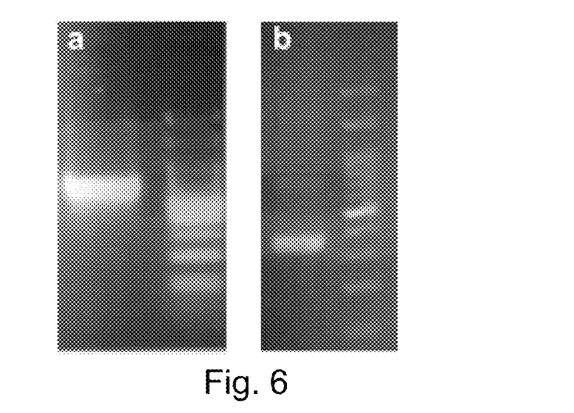
FIG. 6 shows the result of agarose electrophoresis (photograph) of a PCR product.
Figure 7:
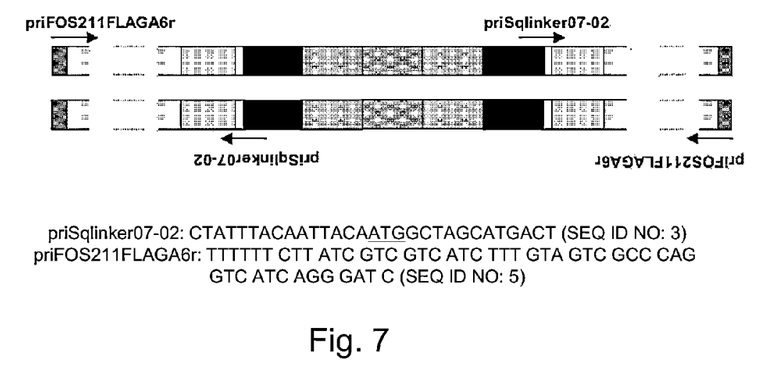
FIG. 7 shows a schematic diagram showing the region amplified with the primers priSqlinker07-02 and priFOS211FLAGA6 and the nucleotide sequences of priSqlinker07-02 and priFOS211FLAGA6 (SEQ ID NOs:3 and 5).

9) However, since the above-described DNA fragment has a palindrome sequence as the whole molecule, determination of the nucleotide sequence by DNA sequencing was carried out after PCR using the above PCR product as a template and priSq0702, which is composed of a part of Sqlinker09, and priFOS211FLAGA6r as primers (FIG. 7). The length of the DNA fragment obtained by this PCR is expected to correspond to about one half of the length of the above-described DNA. The result of electrophoresis of this PCR product is shown in FIG. 6b. A DNA fragment having a size of 300 to 400 bp was obtained as expected.

Figure 8:
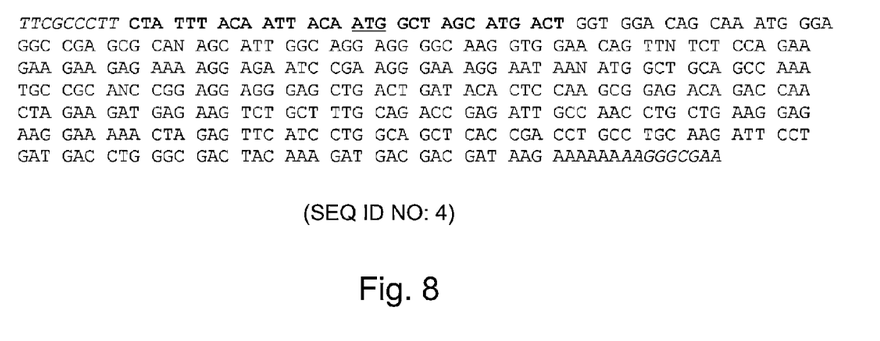
FIG. 8 shows the result of determination of the nucleotide sequence of the DNA fragment obtained in Example 1 by DNA sequencing (SEQ ID NO:4).

10) The DNA fragment obtained as described above was cloned (Invitrogen, PCR-TOPO), and its nucleotide sequence was determined by DNA sequencing. The result is shown in FIG. 8. The part shown in italics corresponds to a sequence derived from the vector. The boldface letters indicate a sequence derived from Sqlinker09 or priSqlinker07-02. The 5'-end of Sqlinker09 and the 3'-end of the F gene cDNA were confirmed to have been correctly linked to each other at the border between T and G of the ACTGGT region. Taking into account the results of 8), 9) and 10) described above in combination, it can be deduced that the DNA fragment shown in FIG. 2h or FIG. 7 was obtained.

TABLE 1

| Lane | 1 | 2 | 3 | 4 | 5 | 6 | 7 | 8 | 9 |
|---|---|---|---|---|---|---|---|---|---|
| 10 × buffer | 5 μl | 5 μl | 5 μl | 5 μl | 5 μl | 5 μl | 5 μl | 5 μl | 5 μl |
| 2 mM dNTP | 5 μl | 5 μl | 5 μl | 5 μl | 5 μl | 5 μl | 5 μl | 5 μl | 5 μl |
| priFOS211FLAGA6r | 10 μl | 5 μl | 1 μl | 10 μl | 5 μl | 1 μl | 10 μl | 5 μl | 1 μl |
| Sample | 10 μl | 10 μl | 10 μl | 1 μl | 1 μl | 1 μl | 0.1 μl | 0.1 μl | 0.1 μl |
| Vent DNA Polymerase | 1 μl | 1 μl | 1 μl | 1 μl | 1 μl | 1 μl | 1 μl | 1 μl | 1 μl |
| DEPC water | 19 μl | 24 μl | 28 μl | 28 μl | 33 μl | 37 μl | 29 μl | 34 μl | 38 μl |

Figure 5:
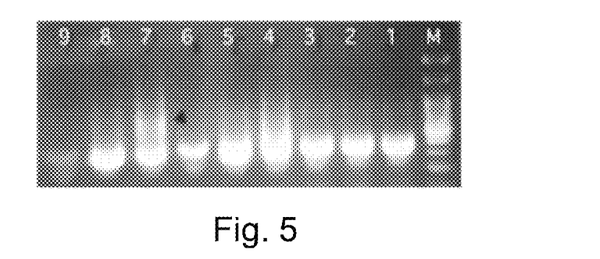
FIG. 5 shows the result of agarose electrophoresis (photograph) of a PCR product.

7) The PCR product was subjected to electrophoresis. The result was as shown in FIG. 5. The intense band of the DNA marker corresponds to 500 bp. In each of the samples in lanes 1 to 8, an intense DNA band at 300-400 bp was observed. This corresponds to the F gene DNA (397 bp). If synthesis of the DNA fragment shown in FIG. 2h is successful, the length of the DNA fragment is expected to be twice as long as this length. It is thought that the reason why the DNA fragment corresponding to monomer F gene DNA was obtained is that unreacted Sqlinker09 contained in the sample acted as a primer to amplify the region between Sqlinker09 and priFOS211FLAGA6r. In view of this, in order to reduce carry-over of Sqlinker09, the amount of the sample was reduced (lanes 7, 8 and 9) or the amount of addition of priFOS211FLAGA6r was increased (lanes 1, 4 and 7) in an attempt to increase the probability of amplification of the DNA fragment between priFOS211FLAGA6r. As a result, a DNA fragment having a length of 700 to 800 bp was obtained in lane 7 as a faint band (indicated by the arrowhead).

Figure 9:
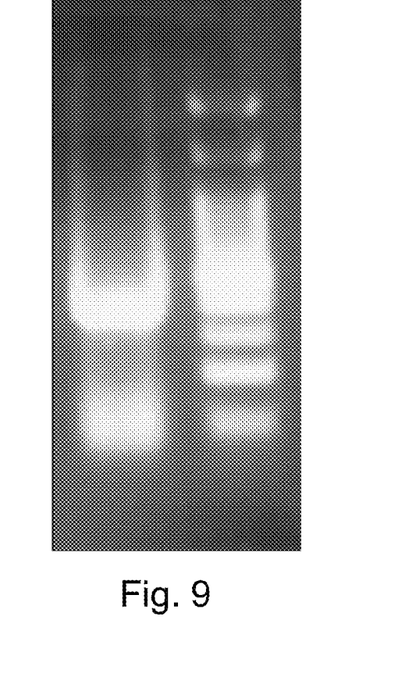
FIG. 9 shows the result of agarose electrophoresis (photograph) of a PCR product.

8) This PCR product was excised from the gel, purified, and then used as a template for PCR. The reaction solution contained KOD Plus ver. 2 buffer, dNTP, MgSO$_4$, priFOS211FLAGA6r, KOD Plus (TOYOBO), template DNA and DEPC water. The thermal cycler was operated with the following program: 30 cycles of 94° C. for 30 seconds, 56° C. for 30 seconds and 68° C. for 1 minute. The result of electrophoresis of the obtained PCR product is shown in FIG. 6a. By using only priFOS211FLAGA6r as a The reaction was carried out in the same manner as in the above square reaction except that the amount of F gene mRNA was changed from 20 pmol to 2 pmol. In this case, no band was obtained at 700 to 800 bp (FIG. 9).

In this Example, the mRNA concentration at which the square reaction was successful was 2 μM, and the mRNA concentration at which the reaction was unsuccessful was 0.2 μM. This indicates that, at an IVV molecule concentration of not less than 2 μM, cDNA dimers are obtained due to the complementarity between the mRNA portion of the IVV molecule and the linker even without a protein-protein interaction. On the other hand, in cases where the IVV concentration is set to not more than 0.2 μM to perform the square reaction, there is a possibility that synthesis of the cDNA dimers due to the complementarity in the nucleic acid portions is not observed and a protein-protein interaction can therefore be detected. That is, a protein-protein interaction having a binding strength of: Kd=not more than $2 \times 10^{-7}$ can be detected under the present experiment conditions.

Example 2

(1) Confirmation of Linkage Between Linker and cDNA

Figure 11:
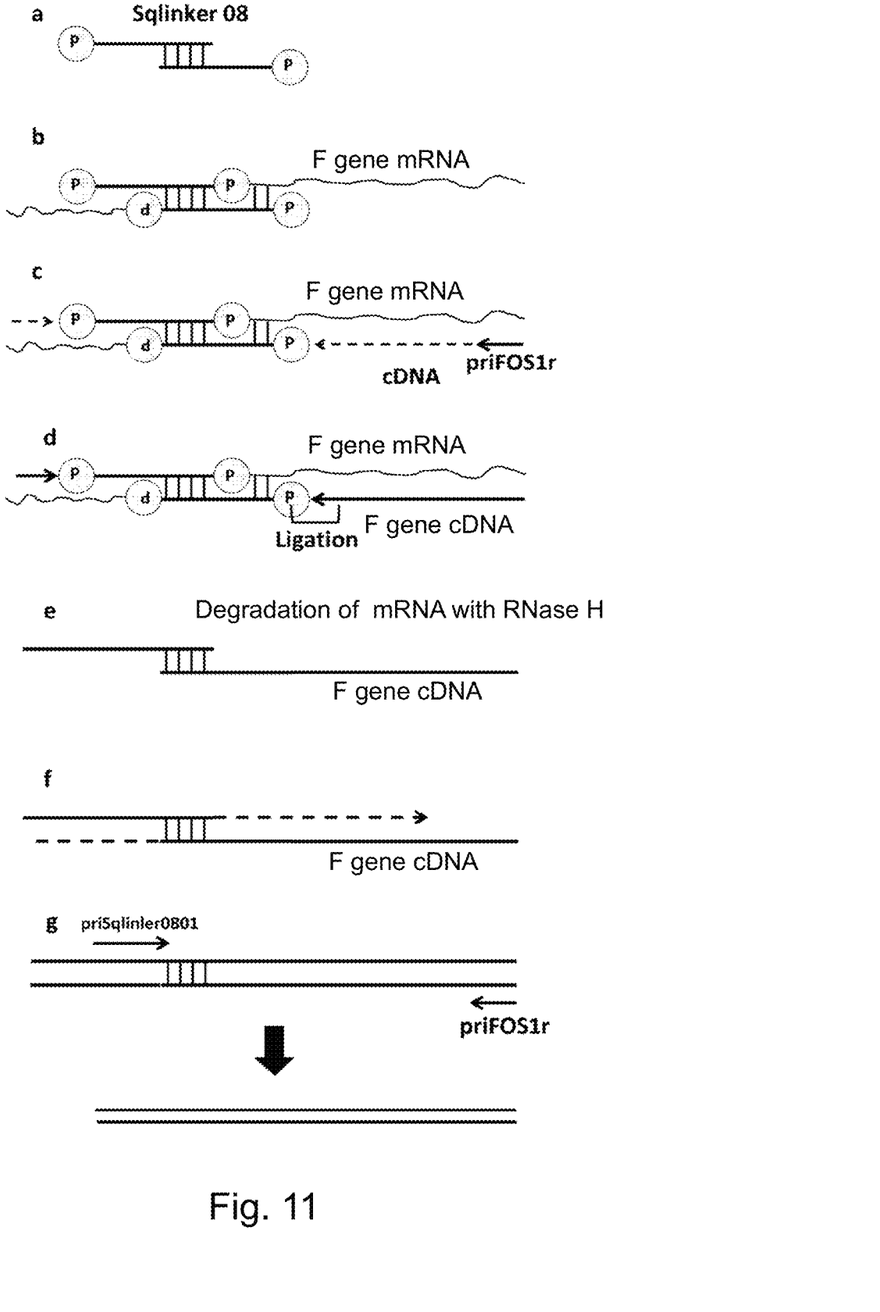
FIG. 11 is a diagram for describing the method of Example 2.

A single-stranded oligo DNA having a self-complementary sequence (designated Sqlinker08, manufactured by FASMAC Co., Ltd.) was used as a linker (FIG. 10a, SEQ ID NO:6). Sqlinker08 had a phosphate group at the 5'-end. First, self-hybridization of Sqlinker08 was performed. With 5 µl of 100 µM Sqlinker08, 10 µl of 10×T4 RNA Ligase buffer (manufactured by Takara Bio Inc.) and 18 µl of DEPC water were mixed, and the resulting mixture was heated at 95° C. for 3 minutes, followed by gradually cooling the mixture to 68° C. (FIG. 11a). To the mixture, 6 µl of 1.6 pmol/µobtained by transcription of the F gene (the leucine zipper region of the FOS gene, see Example 1) and 7 µl of 1.5 pmol/µl mRNA obtained by transcription from J gene (the leucine zipper region of the JUN gene, see Example 1) were added, and the resulting mixture was cooled to 15° C. The mRNAs had a phosphate group at their 5'-ends. Sqlinker08 had a sequence complementary to the SP6 promoter and S2 sequence in the F gene. Subsequently, 12.5 µl of T4 RNA ligase (manufactured by Takara Bio Inc.) was added, and ligation reaction was carried out at 15° C. overnight (FIG. 11b). This reaction solution contained 6 µl of 10 nmol/µl PEG 2000, 3 µl of 0.1M DTT, 1 µl of 40 mM ATP, 20 µl of DMSO, 20 µl of the BSA solution attached to the enzyme, 2 µl of an RNase inhibitor and 4.24 µl of DEPC water. After completion of the ligation reaction, the product was recovered by ethanol precipitation. The result of the ligation reaction was confirmed by electrophoresis.

Thereafter, reverse transcription reaction was performed (FIG. 11c). The reaction solution contained 5 pmol RNA, 20 µM primer (priFOS1r, FIG. 1b, SEQ ID NO:7), 5× attached buffer, 12.5 µl of 2 mM dNTP and 15.5 µl of DEPC water. The reaction solution was heated at 95° C. for 30 seconds and then gradually cooled to 50° C. The reaction solution was then left to stand for 3 minutes, and 5 µl of M-MLV RTase (manufactured by Promega KK) was added to the solution. The reaction solution was left to stand at 50° C. for 1 hour, and then purified through a gel filtration spin column (manufactured by Bio-Rad, Micro Bio-Spin 6 Chromatograpy Columns).

The cDNA portion synthesized by reverse transcription was ligated to the linker portion using Ligation high ver. 2 (Toyobo Co., Ltd.). In this step, 50 µA of the purified reverse transcription product and 50 µl of Ligation high ver. 2 were mixed with each other, and the resulting mixture was subjected to ligation reaction at 16° C. overnight (FIG. 11d). Subsequently, 10 µl of RNase H (manufactured by Invitrogen) was added to the reaction solution to degrade the RNA portion of RNA/cDNA (FIG. 11e).

To the above reaction product, the linker was added to perform extension reaction (FIG. 11f). The reaction solution contained 5 µl of 10×KOD Plus 2 ver. 2 buffer, 5 µl of 2 mM dNTP, 3 µl of 25 mM MgSO$_4$, 1 µl of 20 µM linker as a primer, 1 µl of the ligation reaction product, 1 µl of KOD Plus (manufactured by Toyobo Co., Ltd.), and 34 µl of DEPC water. The reaction was performed at 94° C. for 1 minute 30 seconds and at 68° C. for 3 minutes.

Thereafter, PCR was performed (FIG. 11g). The reaction solution for the PCR contained 5 µl of 10×KOD Plus 2 ver. 2 buffer, 5 µl of 2 mM dNTP, 3 µl of 25 mM MgSO$_4$, 1 µl each of 20 µM forward primer (priSqlinker0801f, FIG. 10c, SEQ ID NO:8) and 20 µM reverse primer (priFOS1r), 1 µl of the extension reaction product, 1 µl of KOD Plus (manufactured by Toyobo Co., Ltd.) and 33 µl of DEPC water. The reaction conditions were: 94° C. for 1 minute, followed by 35 cycles of 94° C. for 30 seconds, 58° C. for 30 seconds and 68° C. for 1 minute. By analysis of the obtained sample by agarose electrophoresis, a band having a size corresponding to about 200 bases could be obtained. This region was excised from the gel and cloned, followed by determination of its nucleotide sequence. The sequence is shown in FIG. 10d. From this result, it can be seen that the linker portion was correctly linked to the SP6 promoter portion in the F gene (although the bases indicated by sloped lines were deleted for unknown reasons). From the above analysis, linking of the linker and the cDNA could be confirmed.

(2) Study on Method of Purification of IVV Molecules from Cell-Free Translation System

[Construction of IVV Molecules Corresponding to FOS and JUN Interaction Regions]

Figure 12:
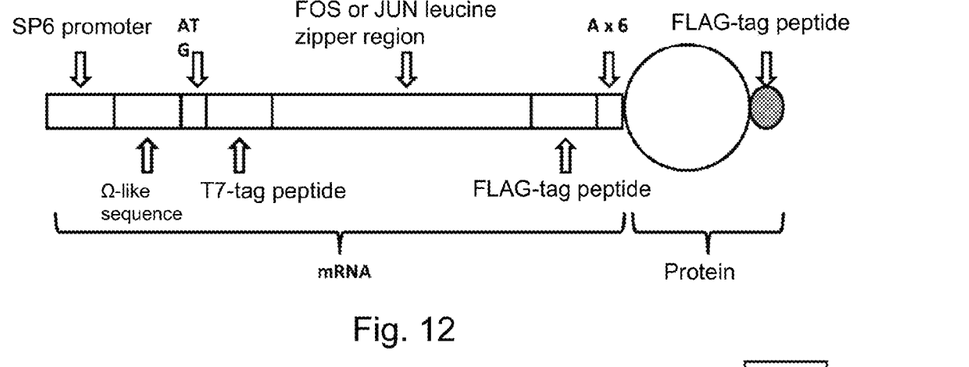
FIG. 12 is the structure of the IVV molecule constructed in Example 2.

As IVV molecules, the interaction regions of FOS and JUN were used. The structures of these structural genes, methods of their construction and transcription reaction into RNA were as described in Example 1. The obtained RNA molecules and a spacer puromycin (p(dCp)$_2$T(FI)$_p$PEG (2000)$_p$(dCp)$_2$ Puro; wherein the symbols are as defined in WO 02/48347) were ligated to each other using T4 RNA ligase (manufactured by Takara Bio Inc.) according to the method described in Example 1 of WO 02/48347. The ligation reaction was performed at 25° C. for 1 hour. The ligation product was purified using RNeasy Mini Kit (manufactured by QIAGEN). The purified ligation product was added to the cell-free translation system (Promega KK, Wheat germ plus) and translation was performed, to synthesize IVV molecules (FIG. 12). The composition of the cell-free translation reaction solution contained 40 µl of wheat germ extract, 1.3 µl of RNasin Plus RNase Inhibitor (Promega KK) and 5 pmol ligation product. The translation reaction was performed at 25° C. for 1 hour.

[Purification of IVV Molecules]

To 50 µl of the translation reaction product, 450 µl of TBSTE buffer (50 mM Tris HCl, 150 mM NaCl, 0.2% Tween 20, 10 mM EDTA) was mixed, and the resulting mixture was centrifuged at 15,000 rpm for 10 minutes, followed by collection of the supernatant. To the collected supernatant, 40 µl of a slurry of anti-M2 agarose beads (manufactured by Sigma) was added, to perform affinity purification of the IVV molecules. The affinity purification was carried out by binding reaction between the supernatant and the affinity beads (for 1 hour (4° C.)) followed by washing with 400 µl of TBESTE buffer. As shown in FIG. 12, the protein portion of the IVV molecule had a FLAG-peptide tag attached at the C-terminal side of the amino acid sequence derived from FOS or JUN (see Example 1).

[Reverse Transcription Reaction of IVV Molecules]

Figure 13:
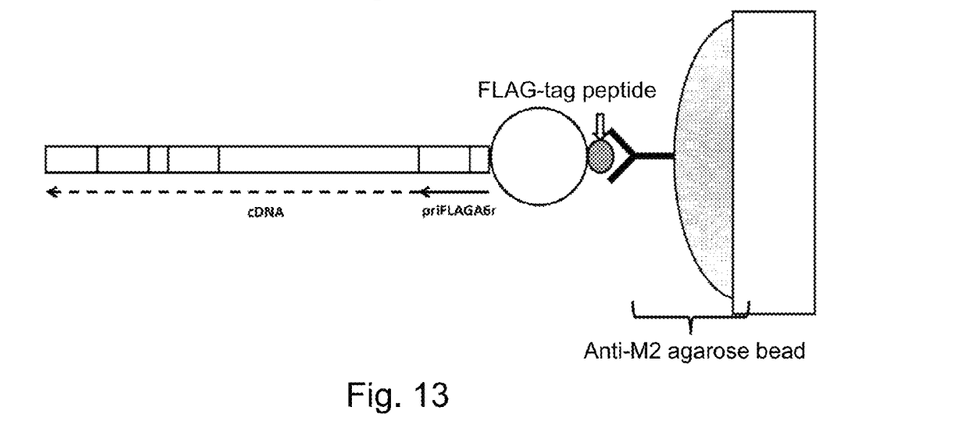
FIG. 13 is a diagram for describing the reverse transcription reaction using an IVV molecule bound to a bead as a template.

The purified IVV molecules were reverse-transcribed. The reverse transcription reaction solution contained the buffer attached to the reverse transcription kit; dNTP mix; M-MLV reverse transcriptase RNase H minus, point mutant; and priFLAGA6r (FIG. 10e). This reaction solution was added to the purified beads, and the reaction was allowed to proceed at 37° C. for 1 hour (FIG. 13).

Figure 14:
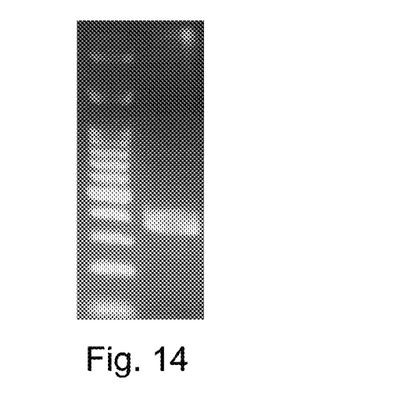
FIG. 14 shows the result of agarose electrophoresis (photograph) of a PCR product.

Since the reverse transcription reaction solution contained DTT, the anti-M2 antibody bound to the beads are denatured during the reverse transcription reaction, and the IVV molecules are detached from the beads. Therefore, by purifying this mixture by gel filtration through a spin column (manufactured by BIO-RAD, Micro Bio-Spin 6 Chromatograpy Columns), IVV molecules where the mRNA portion is hybridized with the cDNA can be recovered (see Matsumura et al., FASEB J., 24, 2201-2210, 2010). Also in the present Example, the hybridized IVV molecules were recovered by this method. Occurrence of the reverse transcription reaction, formation of the hybridized IVV molecules and recovery of the molecules were confirmed by performing PCR using 1 µl of the recovered solution as a template (FIG. 14).

When the reverse transcription reaction was not performed, such a band could not be obtained at all.

In Example 2, linking between the linker and the cDNA could be confirmed by analysis of the nucleotide sequence. Further, for performing the IVV square method, purification of IVV molecules from the cell-free translation system containing contaminants that inhibit reverse transcription reaction is necessary. It was confirmed that the purification can be carried out as described above by the method using a FLAG-tag attached to the peptide portion of the IVV molecule.

INDUSTRIAL APPLICABILITY

By the present invention, a method for analyzing biomolecular interactions, which method can be carried out without performing affinity selection using an immobilized bait, is provided.

What is claimed is:

1. A DNA linker comprising:
    a) a 5' first region comprising the nucleotide sequence of residues 19 to 62 of SEQ ID NO:2 and optionally residues 1-18 of SEQ ID NO:2, and
    b) a 3' second region having 10 to 35 base pairs that is self-complementary, wherein the DNA linker is capable of forming a dimer in solution by base pairing of the 3' second region of the DNA linker with a Tm of 22 to 72° C., and
    wherein the DNA linker is phosphorylated at the 5'-end.

2. The DNA linker according to claim 1, wherein the first region comprises the nucleotide sequence of residues 1 to 62 of SEQ ID NO:2.

* * * * *

SEQUENCE LISTING

```
<160> NUMBER OF SEQ ID NOS: 10

<210> SEQ ID NO 1
<211> LENGTH: 88
<212> TYPE: DNA
<213> ORGANISM: Artificial sequence
<220> FEATURE:
<223> OTHER INFORMATION: synthetic construct; primer priSP6O'fT7FOS117f

<400> SEQUENCE: 1
gaatttaggt gacactatag aaacaattac tatttacaat tacaatggct agcatgactg      60
gtggacagca aatgggaggc cgagcgca                                        88

<210> SEQ ID NO 2
<211> LENGTH: 78
<212> TYPE: DNA
<213> ORGANISM: Artificial sequence
<220> FEATURE:
<223> OTHER INFORMATION: synthetic construct; linker Sqlinker09

<400> SEQUENCE: 2
accagtcatg ctagccattg taattgtaaa tagtaattgt ttctatagtg tcacctaaat      60
tcggcgcgcc ggcgcgcc                                                   78

<210> SEQ ID NO 3
<211> LENGTH: 30
<212> TYPE: DNA
<213> ORGANISM: Artificial sequence
<220> FEATURE:
<223> OTHER INFORMATION: synthetic construct; primer priSqlinker07-02

<400> SEQUENCE: 3
ctatttacaa ttacaatggc tagcatgact                                      30

<210> SEQ ID NO 4
<211> LENGTH: 378
<212> TYPE: DNA
<213> ORGANISM: Artificial sequence
<220> FEATURE:
<223> OTHER INFORMATION: synthetic construct; Amplified product
<220> FEATURE:
<221> NAME/KEY: misc_feature
<222> LOCATION: (69)
<223> OTHER INFORMATION: n = a, t, g, or c
<220> FEATURE:
<221> NAME/KEY: misc_feature
<222> LOCATION: (102)
<223> OTHER INFORMATION: n = a, t, g, or c
<220> FEATURE:
<221> NAME/KEY: misc_feature
<222> LOCATION: (150)
<223> OTHER INFORMATION: n = a, t, g, or c
<220> FEATURE:
<221> NAME/KEY: misc_feature
<222> LOCATION: (173)
<223> OTHER INFORMATION: n = a, t, g, or c

<400> SEQUENCE: 4
```

```
ttcgcccttc tatttacaat tacaatggct agcatgactg gtggacagca aatgggaggc    60
cgagcgcana gcattggcag gaggggcaag gtggaacagt tntctccaga agaagaagag   120
aaaaggagaa tccgaaggga aaggaataan atggctgcag ccaaatgccg canccggagg   180
agggagctga ctgatacact ccaagcggag acagaccaac tagaagatga gaagtctgct   240
ttgcagaccg agattgccaa cctgctgaag gagaaggaaa aactagagtt catcctggca   300
gctcaccgac ctgcctgcaa gattcctgat gacctgggcg actacaaaga tgacgacgat   360
aagaaaaaaa agggcgaa                                                 378
```

<210> SEQ ID NO 5
<211> LENGTH: 49
<212> TYPE: DNA
<213> ORGANISM: Artificial sequence
<220> FEATURE:
<223> OTHER INFORMATION: synthetic construct; primer priFOS211FLAGA6r

<400> SEQUENCE: 5

```
tttttcttta tcgtcgtcat ctttgtagtc gcccaggtca tcagggatc               49
```

<210> SEQ ID NO 6
<211> LENGTH: 42
<212> TYPE: DNA
<213> ORGANISM: Artificial sequence
<220> FEATURE:
<223> OTHER INFORMATION: synthetic construct; linker Sqlinker 08

<400> SEQUENCE: 6

```
ttgtttctat agtgtcacct aaattcggcg cgccggcgcg cc                      42
```

<210> SEQ ID NO 7
<211> LENGTH: 26
<212> TYPE: DNA
<213> ORGANISM: Artificial sequence
<220> FEATURE:
<223> OTHER INFORMATION: synthetic construct; primer priFOS1r

<400> SEQUENCE: 7

```
catcttattc ctttcccttc ggattc                                        26
```

<210> SEQ ID NO 8
<211> LENGTH: 27
<212> TYPE: DNA
<213> ORGANISM: Artificial sequence
<220> FEATURE:
<223> OTHER INFORMATION: synthetic construct; primer priSqlinker0801f

<400> SEQUENCE: 8

```
ttgtttctat agtgtcacct aaattcg                                       27
```

<210> SEQ ID NO 9
<211> LENGTH: 241
<212> TYPE: DNA
<213> ORGANISM: Artificial sequence
<220> FEATURE:
<223> OTHER INFORMATION: synthetic construct; Amplified product

<400> SEQUENCE: 9

```
ttgtttctat agtgtcacct aaattcggcg cgccggcgcg ccgaatttag gtgacactat    60
agaaacaaga atttaggtga cactatagaa acaattacta tttacaatta caatggctag   120
catgactggt ggacagcaaa tgggaggccg agcgcagagc attggcagga ggggcaaggt   180
```

```
ggaacagtta tctccagaag aagaagagaa aaggagaatc cgaagggaaa ggaataagat        240
g                                                                       241

<210> SEQ ID NO 10
<211> LENGTH: 30
<212> TYPE: DNA
<213> ORGANISM: Artificial sequence
<220> FEATURE:
<223> OTHER INFORMATION: synthetic construct; primer priFLaga6r

<400> SEQUENCE: 10
tttttcctta tcgtcgtcat ctttgtagtc                                        30
```